United States Patent [19]

Shimodaira et al.

[11] 4,256,573
[45] Mar. 17, 1981

[54] PROCESS FOR BIOLOGICAL TREATMENT OF WASTE WATER IN DOWNFLOW OPERATION

[75] Inventors: Chiaki Shimodaira, Kanagawa; Yoshinori Yushina, Musashino; Hiroshi Kamata, Tokyo; Hideo Komatsu, Mitaka; Akinori Kurima, Yokohama; Osamu Mabu, Kawasaki; Yoshiharu Tanaka, Kanagawa, all of Japan

[73] Assignee: Chiyoda Chemical Engineering and Construction Co., Ltd., Yokohama, Japan

[21] Appl. No.: 12,246

[22] Filed: Feb. 14, 1979

[30] Foreign Application Priority Data

Feb. 14, 1978 [JP] Japan ................................. 53-15650

[51] Int. Cl.$^3$ ............................................... C02F 3/08
[52] U.S. Cl. .................................... 210/618; 210/625; 210/630
[58] Field of Search ..................... 210/17, 3, 8, 20, 16

[56] References Cited
U.S. PATENT DOCUMENTS

| | | | |
|---|---|---|---|
| 3,846,289 | 11/1974 | Jeris et al. ................................. | 210/8 |
| 3,933,629 | 1/1976 | Smith et al. ............................ | 210/17 |
| 3,966,599 | 6/1976 | Burkhead ............................ | 210/17 X |
| 4,009,099 | 2/1977 | Jeris et al. ............................ | 210/17 X |
| 4,115,266 | 9/1978 | Ohshima ............................ | 210/20 X |
| 4,126,544 | 11/1978 | Baensch et al. ..................... | 210/17 X |

*Primary Examiner*—Thomas G. Wyse
*Attorney, Agent, or Firm*—Armstrong, Nikaido, Marmelstein & Kubovcik

[57] ABSTRACT

This invention relates to biological treatment of waste water using a carrier floatable on water, and more particularly to a novel process for treatment of waste water utilizing a fluidized bed which is formed by supplying waste water in a downflow operation. The process for treatment of waste water of this invention is applicable to both anaerobic and aerobic biological treatment. A good example of the former anaerobic biological treatment to which this invention is applicable is the process wherein the nitrate or nitrite nitrogen which is one of the nitrogen compounds that are at present believed to be one cause of the eutrophication in rivers, lakes, seas, etc. is treated with denitrifying bacteria in an anaerobic condition to be released in the form of nitrogen gas, and the typical of the latter aerobic treatment is the practice in the utilization of the action of the aerobic bacteria which can oxidize organic substances in sewage, industrial waste waters, etc.

7 Claims, 5 Drawing Figures

PROCESS FOR BIOLOGICAL TREATMENT OF WASTE WATER IN DOWNFLOW OPERATION

BACKGROUND OF THE INVENTION

Among the processes for treatment of waste water utilizing microbes are the process of suspended microbes as heretofore represented by activated sludge process, and the process of fixing the microbes by attaching them to stones, plates, plastics, etc. as encountered in the trickling filter, rotating disc filter, etc., and it is well known that all these processes have been in wide use. Further, in recent years there has been investigated a process utilizing fine particle carrier to which microbes have been attached. The most characteristic features in the application of fine particle carrier to the biological treatment are (1) that the concentration of the microbes may be taken to be extremely high, (2) that the specific surface area of the carrier becomes large, (3) that as the result the rate of reaction per unit volume of reactor can be increased so high that the viological reactor can be designed compact, (4) that especially when the microbial concentration has been taken to be high, it is very easy to separate the microbes from the liquid, although such a separation has heretofore been considerably difficult, and so on.

DESCRIPTION OF THE PRIOR ART

For the above described reasons the process for treatment of waste water using the fine particle carrier to which microbes have been attached has the advantages that are not seen in the existing processes of microbe suspended or fixed type. On the other hand, however, such a process for treatment of waste water using fine particle carrier to which microbes have been attached requires a specially devised apparatus in order to obtain the full achievement of its effect. That is to say, in order that the biological treatment may exhibit the above described characteristic features, the following requirements may be mentioned: (1) that the fine particle carrier should have a particle surface to which microbes can easily attach, (2) that adhesion, cohesion, or association should not occur among the fine particles themselves, (3) that the waste water uniformly contacts with the fine particle carrier without channeling, (4) that the growth and sloughing of the microbes attached to the surfaces of the fine particle carrier should be balanced so that the film thickness is maintained constant, (5) that when denitrification is proceeding by the attachment of the denitrifying bacteria which generate nitrogen gas, the fine particle carrier to which microbes have been attached should not over flow from the system, being caused by the generating gas bubbles, (6) that upon the aerobic microbial treatment the fine particle carrier should not outflow from the system, being caused by the aeration for the oxygen supply, (7) that in order to ensure the smooth progress of the substrate removal reaction, water and the carrier to which microbes have been attached should be maintained in moderate fluidization, and so on.

As the apparatus for biological treatment using fine particle carrier, which can satisfy these requirements, one can consider an apparatus with a fixed bed of particulate carrier, an apparatus of the type of completely mixing particulate carrier, an apparatus with a fluidized bed of particulate carrier, etc., but according to the basic experiments carried out by the present inventors it was found that all these apparatuses have the following merits and demerits.

The first named apparatus with a fixed bed of particulate carrier uses sand, activated carbon, anthracite, etc. as the particulate carrier whose specific gravity is larger than 1.0, and allows the microbial reaction to proceed while the upwardly or downwardly flowing waste water is passing through the fixed bed. The demerit of this apparatus is found in that since the fixed bed is formed by particulate carrier the fixed bed is readily plugged by the growth of the microbes. The plugging brings about the channeling of the waste water as well as the increased pressure loss, so that usually it becomes necessary to carry out the periodical washing of the particulate carrier.

The second named apparatus of the type of completely mixing particulate carrier is an apparatus much resembling an aeration tank in the conventional activated sludge process, in which the particulate carrier is used in a completely mixed state, and in order to ensure the complete mixing in the system it requires stirring and aerating means, so that it has a disadvantage that especially when the specific gravity and the concentration of the particulate carrier become larger, an extremely large power is required for the maintenance of the complete mixing in the system. Moreover, if the particulate carrier is suspended in such a mixed state with violent stirring the shearing of the attached microbes or the fracture of the particulate carrier is caused, failing to exhibit the above described characteristic features that are the object of the process for treatment of waste water using the microbe-attached carrier. However, the process of the above described type is characterized in that even when the raw water shows quality fluctuation as well as flow rate fluctuation, water of comparatively stable water quality can be obtained, so that it has an advantage that if the specific gravity and the amount of the particulate carrier used are limited the characteristic features in the use of the particulate carrier can be exhibited to a certain degree.

Next, the third named apparatus with a fluidized bed of particulate carrier is usually of a vertically elongated shape. When the particulate carrier packed is given a linear velocity more than the minimum required for the fluidization, the bed of the particulate carrier expands, and maintaining a definite height of the expanded bed, each particle begins to be fluidized in up and down, right and left, or rotating motion, under which conditions the waste water and the microbes on the particulate carrier are brought in contact. As the kind of the particulate carrier now used in the apparatus of fluidized bed type there may be mentioned activated carbon, sand, anthracite, plastics, etc.

As compared with the first and second apparatuses the apparatus of fluidized bed type has the following advantages. That is to say, since in the apparatus of this type the particulate carrier is in fluidization by virtue of the linear velocity of water more than the minimum fluidization velocity, even in the special case where the apparatus is equipped with a strring means the power is less required than the apparatus of the type of completely mixing, and also the motion of the particles is so gentle and the growth of microbes on their surfaces is so ready that the microbes can be carried thereon in high concentrations. Further, differing from the first apparatus of fixed bed type no problem of plugging arises. Since the height of the packed bed of particulate carrier can be readily varied by varying the velocity of the water, and hence the concentration of the microbes also can be varied. In addition to the above, the microbes grown on the surfaces of the particulate carrier can be sloughed off therefrom when the microbial films of an almost definite thickness have been formed either by the mutual collision of the particles due to the fluidization or by the gentle motion of the stirring impellers, and so on.

On the other hand, however, in the apparatus of the conventional fluidized bed type in an upflow operation using activated carbon, sand, anthracite, plastics, etc. it is difficult to obviate the following deficiencies. That is to say, for instance, when it is utilized as an apparatus for an aerobic denitrification, the generating nitrogen gas attaches to the microbes on the surfaces of the particulate carrier, and as a result a phenomenon arises such that as if a floatation process were carried out by the aid of a gas, the particulate carrier floats on the water and outflows from the system. This phenomenon readily takes place by the causes rendering the gas generation violent, such as a temperature rise, an increase in the nitrogen loading due to the change in the nitrogen concentration, etc. and in an extreme case it even happens that all of the particulate carrier packed outflows from the system.

Also, when the apparatus is utilized as one for aerobic microbial treatment the following deficiencies have been found. Heretofore, the oxygen source required for the aerobic microbes was resorted to the process in which finely divided air bubbles are formed by passing compressed air through a diffuser plate or pipe so that oxygen may be dissolved effectively in water, but when the finely divided air bubbles are supplied to the lower part of the bed of the particulate carrier the expanded bed of the particulate carrier is inevitably led to confusion which disperses the particulate carrier throughout the whole system approaching a completely mixed state, and also, at the same time the particulate carrier outflows from the system. Although the confusion of the fluidized bed depends on the amount of the air supplied as well as the diameter of the bubbles, from the practical view point of maintaining the fluidized bed stationary it is very difficult to pass an air directly through the fluidized bed. Therefore, in the case where the apparatus of fluidized bed type is used for the aerobic biological treatment, the more preferable process is such that dissolved oxygen is sufficiently supplied to water outside the system and the water thus treated is introduced in the system.

As above described the conventional apparatus with fluidized bed in an upflow operation has many advantages but at the same time it presents also several problems such that the particulate carrier outflows from the system, its application to the aerobic biological treatment is difficult, and so on.

SUMMARY OF THE INVENTION

The present inventors have, for the past three years or more, made the experiments on the anaerobic denitrification and the aerobic biological treatment using particulate material as the carrier, including various apparatuses as above described, and as the result they could find out a novel process which can utilize the particulate carrier in a very state close to nature, unlike the above described apparatuses of various kinds.

The process for biological treatment using particulate material in this invention may be considered to come within the category of the above described fluidized bed type in a broader sense, but the process of this invention is characterized by that the particulate carrier which has an apparent specific gravity smaller than the specific gravity of water and moreover can float on the water is packed in a system, and by supplying waste water in a downflow operation onto the upper portion of the bed which is formed by the particulate carrier rising to the surface of water the bed of the particulate carrier is fluidized so as to effect the contact in an efficient manner. At first sight the process of this invention may be regarded in the same light as the fluidized bed system in an upflow operation which was turned upside down, but it is no exaggeration to say that the process of this invention is an extremely unique and novel process which can solve at a stroke all the problems the process using any of the above described three kinds of apparatuses could not solve. In other words, the carriers which distinctly sink in water and have an apparent specific gravity larger than 1.0 such as activated carbon, sand, anthracite, plastics, etc. that are used in the conventional fluidized bed involve the most difficult problems such that the generation of gas bubbles resulting from the microbial reactions or the intermingling of a gaseous material into the system by supplying air or oxygen required from the aeration brings about the obvious confusion of the fluidized bed as well as the particulate carrier outflows from the system. In accordance with the biological treatment of this invention, however, all these problems can be completely overcome as later described by virtue of the use of light carriers which can float on the water.

Now, the process of this invention will be explained more fully below. First, a reactor of a vertically elongated shape is packed with particulate carrier which has an apparent specific gravity smaller than 1.0 and moreover can readily float on the water. When water is charged in this reactor, the particulate carrier forms a bed whose height from the water surface varies depending on the volume of the particulate carrier packed, in which case the bottom of the reactor is occupied by water alone because the particulate carrier rises to the upper part. The waste water to be treated is supplied to the reactor from the top so as to form a downflow. The particulate carrier shows various motions depending on the linear velocity of the water. That is to say, when the linear velocity is low, the particulate carrier remains immobile as if it were in a fixed bed, but as the linear velocity increases, the bed of the particulate carrier expands, and by further increase in the linear velocity it begins to be fluidized. In the case where the particulate carrier has a wide particle size distribution, even if the water is supplied at a definite linear velocity, it will be observed that the particulate carrier in the reactor is in such a state that a fixed bed is formed in the upper part, an expanded bed is formed in the middle part, and a distinct fluidized bed is formed in the lower part.

When the recirculation of water in the reactor is carried out for about two weeks after the waste water has been inoculated with the seeding bacteria, it will be found that the microbes attach to the surface of the particulate carrier and grow thereon. Since the microbes have an apparent specific gravity roughly close to 1, when they attach to the particulate carrier, the apparent specific gravity of the carrier become more or less larger, so that there is found a general tendency that the linear velocity required for the initiation of fluidization becomes smaller. Thus, when the velocity of flow of the waste water fed is maintained constant, the height of the fluidized bed gradually increases. For this reason, once the operation has become a steady state condition, it is desirable to maintain the height of the fluidized bed at a constant value so that the amount of the microbes attached may be constant. For sloughing off the microbes from the particulate carrier the reactor is equipped with a device such as a stirrer, etc. which can impart shearing force to the fluidized bed. Such a device is particularly effective in that since the particulate carrier to which excess microbes have been attached comes down to deposit it can make the carrier refloat by sloughing off the excess microbes therefrom, or that it can prevent the carrier from the mutual bonding and also can promote the floatation of the gas formed by the reaction.

In the anaerobic denitrification, since the nitrate nitrogen in the waste water is reduced to the state of nitrogen gas, it rises up in the form of small bubbles through the fluidized fed. In the conventional process in an upflow operation, the rise of these nitrogen gas bubbles aids in the flotation of the particulate carrier, increasing the amount of the particulate carrier which outflows from the system, being accompanied by the waste water to be treated, so that the removal of these gas bubbles was one of the subjects, but in the process of this invention the rise of these nitrogen gas bubbles favors the formation of the fluidized bed on the contrary because it imparts buoyancy to the particulate carrier by adhering to it when it is being pushed in by the downflow. Also, in the aerobic biological treatment the gas bubbles rising as a result of either dissolving oxygen beforehand in the waste water or introducing an oxygen-containing gas, or most generally air, in the fluidized bed from the lower part during the reaction fulfill the same function as the nitrogen gas bubbles in the anaerobic denitrification. Thus, in accordance with the process of this invention the gas bubbles which were the bottle-neck in the conventional processes produce an extremely desirable effect. Further, in the aerobic biological treatment the air bubbles have in fact a considerably strong shearing action for the microbial films attached to the particulate carrier, but they do not shear all the microbial films completely. In general it is believed that in order to obtain the satisfactory results with the microbial films, 400–500 microns of thickness will suffice, and therefore, in view of the fact that in the process of this invention the excess microbial films can be sheared so that the particulate carrier may always have a definite buoyancy without increasing the specific gravity, the process of this invention is most desirable for controlling the thickness of the microbial films to the above described range.

The method of supplying the waste water to the microbial reactor of this invention is not critical, but it is desirable that the waste water is trickled all over the surface of the floating bed of the particulate carrier, so that the reactor is usually provided with a distribution pipe having a number of orifices above the surface of the carrier and the waste water is uniformly supplied onto the surface of the carrier. The withdrawal of the waste water treated is made beneath the bed of the particulate carrier, but in reality the waste water treated is withdrawn once through a riser-pipe or the like extending up to the level of the upper surface of the carrier.

When use is made of a large quantity of particulate carrier whose bed becomes high in accordance with the process of this invention it is desirable to install a means such as a stirrer, etc. that can impart shearing force so as to prevent the particles from their mutual bonding or keep a passage way for the bubbles.

The particulate carrier used in this invention is the particles having an apparent specific gravity smaller than 1.0, or preferably smaller than 0.9, and those which do not absorb water even in the water are suitable. In general, use is made of the particles consisting of natural materials such as wood, rocks, etc. or artificial materials such as foamed plastics, ping-pong balls and other like hollow bodies. Of these materials the use of inexpensive and lightweight rocks is most desirable from the viewpoint of the economy in the raw material. Among the materials which are now in use as foamed lightweight building materials are particles of several microns—several tens millimeters that can float on the water, and these particles are what are obtained as foamed lightweight product when the rocks rich in vitreous components containing silica, alumina, sodium, potassium, etc. such as represented by, for instance, obsidian, liparite, pitchstone, shale, etc. are pulverized and then calcined until the moisture is gasified. These aggregates which absorb no water are most preferable as the carrier used in the process of this invention. Besides the above, the artificial materials such as represented by foamed plastic particles containing closed pores can also be used as the particulate carrier of this invention. The plastic particles that are capable of artificial processing are adapted for obtaining particles of uniform size, so that they are the best materials in order to carry out a stable prolonged operation. However, generally speaking, it is not desirable that the commercially available plastics whose surface is smooth are used as they are. This is because the microbes attached to such a smooth surface of plastics are very liable to slough off therefrom, so that they cannot be used where friction occurs between particles as in the process of this invention. Thus, when use is made of plastics it is desirable to make them ready for the attachment of the microbes (1) by foaming them so as to form creasy surface, (2) by surface processing plastic particles so as to form rough surface, (3) by bonding particles of native, inorganic, foamy, lightweight material with molten plastics, etc. In order to make the foamed plastic particles with creasy surface, first a foaming agent is added to the raw material of the plastic, and after the resulting mixture has been molded by extrusion molding, etc., the molded product is cut to particle size by means of a cutter. When the raw material in the molten state within the molding machine is extruded out of the molding machine it is cooled and solidified with foaming, whereby an innumerable closed pores are occluded in the interior of the plastic particles, but the surface looks as if it were a crator of a volcano which is creased with wrinkles, and something like plastic fiber is also formed in parts of the surface.

When it is desired to bond some inorganic material with plastic material, the fine particles of the inorganic material are added to the raw material of the plastic containing a foaming agent, a plasticizer, etc. and the resulting mixture is molded by extrusion molding, injection molding, etc. into particles of predetermined size or bars which are cut into particle size by means of a cutter. In the preparation of particles having small specific gravity, use is made of particles of foamed lightweight material such as, for instance, "Shirasu-balloons" (which are hollow glass micro-spheres produced from one kind of volcanic ashes, named "Shirasu"), but in order to approach the specific gravity to 1.0 use is made of the material having large specific gravity such as, for instance, particles of calcium carbonate. Since in this method the plastic material can be used as a binder of the inorganic particles, economically inexpensive floatable particles can be obtained. Further, the particles of the native, inorganic, foamed lightweight material sometimes happen to sink in water owing to the penetration of water thereinto, but by virtue of the bonding and the surface coating of the inorganic material with plastic material the sinking property can be prevented. The particles of the lightweight rocks such as pumice which is distributed in the volcanic region are also usable even without any artificial processing, but those which contain closed pores are preferable to those which contain open pores because of the long lasting floatation.

The anaerobic and aerobic biological treatment in the process of this invention can remove the nitrogen, BOD, and COD contained in waste water in an extremely efficient manner as well as in a high rate of reaction. As the apparatus, in the case where the concentration of the above described substrate is up to several tens ppm, any one of one pass type will suffice to attain the aimed concentration of the substrate, but in the case where the waste water of which the concentration of the substrate is as high as several hundreds–several thousands ppm is to be treated it is also possible to adopt a process wherein portion of the waste water to be treated is circulated until the concentration of the substrate is reduced to the clean level. The method of circulation is not critical, so that either the external circulation by means of a pump, etc. or the internal circulation by means of a draft tube installed in the apparatus may be performed.

As above described, it is obvious that in accordance with this invention the concentration as well as the rate of reaction of the microbes can be maintained extremely high by attaching the microbes to particulate carrier, thereby rendering it possible to minimize the size of the conventional apparatus for biological treatment; the problem of plugging resulting from the use of particulate carrier can be solved; so that the process is applicable to both anaerobic and aerobic cases; and the particulate carrier does not outflow from the system even against the gas generation due to the microbial reaction or the direct supply of air or oxygen, thus all of the largest deficiencies found in the existing techniques being overcome at a stroke.

DESCRIPTION OF THE PREFERRED EMBODIMENT

Now, with reference to the drawings the process of this invention will be explained to make it more understandable below.

Figure 1:
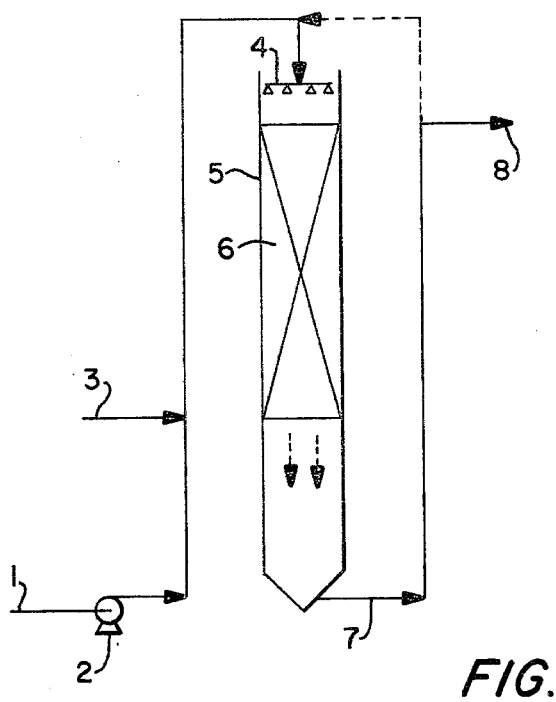
FIG. 1 illustrates one embodiment of the apparatus for anaerobic denitrification treatment.

In FIG. 1, raw water 1 is uniformly trickled into apparatus for anaerobic denitrification treatment 5 from distribution pipe 4 through feed pump for raw water 2. Usually methanol 3 is added on the way to distribution pipe 4 in an amount about 3 times as much as the $NO_3$—N contained in the raw water. Within apparatus 5 particles of foamed lightweight building material having a specific gravity smaller than 1.0 are floating, with the apparatus being filled about ⅔ full by volume of the particles. The waste water is supplied by adjusting the flow rate in such a way that the volume of the particulate carrier usually becomes about 4/5 of the volume of the apparatus, and after having been contacted with microbes the waste water is withdrawn from the lower part 7 of apparatus 5 and discharged from discharging pipe 8.

Figure 2:
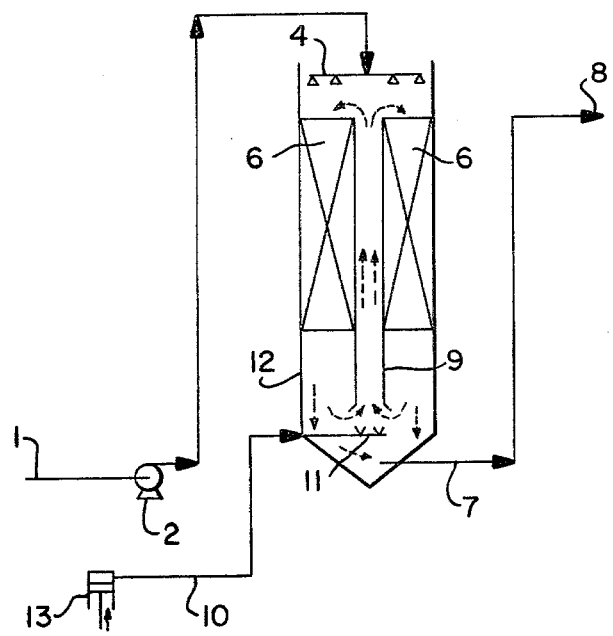
FIG. 2 illustrates one embodiment of the apparatus for aerobic BOD treatment.

In FIG. 2 also, similarly raw water 1 is uniformly trickled into apparatus for aerobic BOD treatment column 12 from distribution pipe 4 through feed pump for raw water 2. Apparatus for aerobic BOD treatment 12 is provided with draft tube 9 in its center, and between draft tube 9 and the outer column of the apparatus the particulate carrier consisting of "Shirasu-balloons" are filled in the state floating on the water. The apparatus is also provided with diffuser 11 beneath draft tube 9, and the compressed air led through pipe 10 from air compressor 13 is released from this diffuser in the form of fine bubbles. These bubbles dissolve in water while they are rising up through draft tube 9 and supply the oxygen required for the treatment by the aerobic bacteria. As a result the flow of water within the draft tube becomes an upflow, which flows into packed bed 6 of particulate carrier along with dissolved oxygen, becoming a downflow, which contacts with the microbes on the particulate carrier. Within the apparatus such circulation of water is repeated. The water treated is withdrawn from the lower part 7 of the apparatus and discharged from discharging pipe 8.

The particles of packed material which come down to the bottom by the excess attachment of microbes slough off their excess microbes while they are rising up through the draft tube.

Further, when an apparatus provided with draft tube 9 is used in the anaerobic treatment, either the gas recovered from the upper space in the sealed treating tank 12 may be circulated for reuse through diffuser 11, or an upflow may be allowed to form within the draft tube by installing, for instance, an impeller, etc. within the draft tube. The excess microbe-attached particles rising up through the draft tube slough off their excess microbes by virtue of the shearing force of the impeller.

Figure 3:
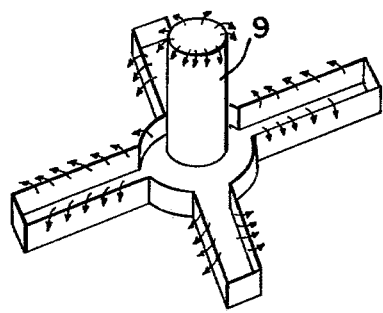
FIGS. 3, 4 and 5 illustrate embodiments of the distributor which are mounted on the upper part of the draft tube in FIG. 2.
Figure 4:
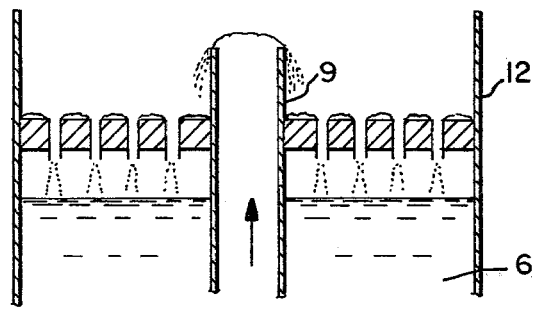
Figure 5:
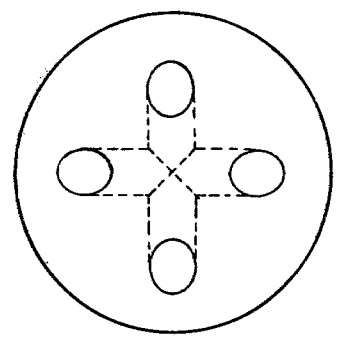
Figure 5:
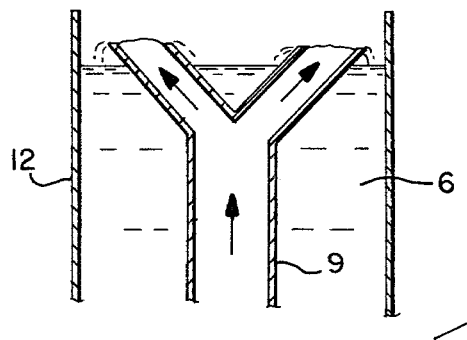

The water to be treated which has risen up through the draft tube can be uniformly distributed by the use of a distributor such as illustrated in FIGS. 3, 4 and 5. FIG. 3 indicates a distributor of trough type, which is widely in common use, when in the state mounted on the upper part of the draft tube. How to assemble the troughs is not critical, so that radial structure, lattice structure, or any other structure will do so far as the water can be uniformly distributed.

FIG. 4 indicates a combination of a draft tube with a distributor in the form of a circular perforated plate equipped with cylindrical tubes. In the figure the diameter of said cylindrical tubes used is large enough so as not to be plugged by the particulate carrier as well as by the sloughed sludge, and it is preferably larger than 3 mm.

Also, FIG. 5 indicates a distributor of manifold structure at the upper end of draft tube 9, with the openings of said manifold being disposed evenly across the upper surface of the reactor.

Some examples of this invention will be shown below. It should be understood however that this invention is not limited to these examples.

EXAMPLE 1

Denitrification of waste water containing $NO_3$—N in low concentrations

Using the apparatus shown in FIG. 1 the BOD and nitrification treatment of sanitary waste water was carried out, whereby the waste water containing $NO_3$—N was subjected to anaerobic denitrification and the $NO_3$—N was released into the atmosphere as nitrogen gas, with the result being shown below. The major apparatus used and the general features of the waste water are as follows:
  Apparatus for anaerobic denitrification: Made of polyvinyl chloride, $3^{in\phi} \times 3.0^{mH}$,
    Volume about 19 liters
  Particulate carrier: Foamed lightweight building material,
    (Trade name: Perlite)
    Average diameter—2 mm
    Packed volume—13 liters
    Bulk density—0.3 g/cc
  Kind of waste water: Sanitary waste water subjected to aerobic treatment
  $NO_3$—N concentration in the water fed: 20–50 ppm
  Circulation of water to be treated: Not performed The flow rate of water was taken to be about 60 l/hr., and the linear velocity of water in the apparatus was about 10 m/hr. This linear velocity guaranteed the gentle fluidization of the particulate carrier. About 5% of the particulate carrier packed settled down on account of the penetration of water and the attachment of microbes, so that these were withdrawn from the system and the remaining floated carrier particles were used in the experiment.

In addition, as the hydrogen donor for denitrication methanol was added to the raw water in an amount 3 times as much as the $NO_3$—N concentration.

The result is shown in Table 1.

TABLE 1

| Raw Water | | | | Water treated | | |
|---|---|---|---|---|---|---|
| Atmospheric temperature (°C.) | pH | $NO_3$—N (ppm) | $NO_2$—N (ppm) | pH | $NO_3$—N (ppm) | $NO_2$—N (ppm) |
| 30 | 7.6 | 51 | — | 9.2 | <1 | — |
| 29 | 7.7 | 47 | 2.3 | 8.8 | <1 | <1 |
| 28 | 7.6 | 45 | 2.3 | 8.8 | <1 | <0.3 |
| 28 | 8.5 | 48 | 2.2 | 9.2 | <1 | <1 |
| 23 | 7.7 | 22 | <0.3 | 8.9 | <1 | <0.3 |
| 26 | 7.2 | 42 | 7 | 9.6 | <1 | <1 |
| — | 9.3 | 40 | 16 | 9.1 | <1 | <0.3 |

EXAMPLE 2

Denitrification of waste water containing $NO_3$—N in high concentrations

Using the same apparatus and particulate carrier as in Example 1 the procedure of Example 1 was repeated except that portion of the water to be treated was circulated.
  Kind of waste water: Artificial waste water containing $NO_3$—N in a high concentration
  $NO_3$—N concentration in the water fed: 1000 ppm, 2000 ppm
  Circulation of the water to be treated: Performed The result is shown in Table 2.

TABLE 2

| Test No. | Raw water $NO_3$—N (ppm) | Inlet of* apparatus $NO_3$—N (ppm) | Water treated $NO_3$—N (ppm) | Circulation rate of water (l/hr) | Raw water feed rate (l/hr) | Circulation ratio |
|---|---|---|---|---|---|---|
| 1 | 2000 | 13.3 | 1.1 | 50.3 | 0.35 | 144 |
| 2 | " | 17.6 | 1.2 | " | 0.48 | 113 |
| 3 | " | 24.1 | 1.2 | " | 0.61 | 83 |
| 4 | " | 30.9 | 1.3 | " | 0.77 | 65 |
| 5 | " | 37.4 | 2.3 | " | 0.86 | 59 |
| 6 | " | 45.5 | 2.5 | " | 0.88 | 57 |
| 7 | " | 47.2 | 2.5 | " | 1.12 | 45 |
| 8 | 1000 | 47.2 | 2.3 | " | 2.36 | 21 |

*Inlet of apparatus: A mixture of the raw water and the water under treatment in circulation is fed from this inlet of apparatus.

The above experiment was carried out by controlling the temperature of water to 27°–31° C. and the pH of the raw water to 7.9–8.0.

In addition, as the hydrogen donor methanol was added to the raw water in an amount 3 times as much as the $NO_3$—N.

EXAMPLE 3

Aerobic treatment of sanitary waste water

Using an apparatus as shown in FIG. 2 the BOD removal by aerobic bacteria of sanitary waste water was experimented.
  Apparatus for aerobic treatment: Made of polyvinyl chloride $5^{in\phi} \times 2.0^{mH}$
    Volume about 35 liters
    Provided with a draft tube
    Draft tube $5^{cm\phi} \times 1.7^{mH}$
  Particulate carrier: "Shirasu-balloons"
    Average diameter—about 0.3 mm
    Packed volume—about 20 liters
    Bulk density—0.2 g/cc
  Kind of waste water: The sanitary waste water treated in a septic tank was used as the raw water.
  BOD of waste water: Shown in Table 3.
  Circulation of the water to be treated: Internal circulation through draft tube by aeration.

The result is shown in Table 3.

TABLE 3

| Flow rate (l/hr) | Raw Water BOD (ppm) | Water temperature (°C.) | pH | Water treated BOD (ppm) | pH | Rate of removal of BOD (%) |
|---|---|---|---|---|---|---|
| 10 | 74 | 15 | 7.6 | 8 | 7.8 | 89.2 |
|  | 96 | 15 | 7.9 | 11 | 7.8 | 88.5 |
|  | 86 | 15 | 7.9 | 9 | 7.9 | 89.5 |
| 20 | 114 | 16 | 8.0 | 21 | 7.9 | 81.5 |
|  | 96 | 16 | 7.4 | 13 | 7.8 | 86.5 |
|  | 76 | 16.5 | 7.6 | 11 | 7.7 | 85.5 |
| 30 | 74 | 17 | 8.2 | 11 | 7.9 | 85.1 |
|  | 74 | 17 | 7.6 | 12 | 7.7 | 83.8 |
|  | 100 | 16 | 8.1 | 23 | 7.8 | 77.0 |
| 40 | 68 | 16.5 | 8.3 | 15 | 8.1 | 77.9 |
|  | 72 | 16 | 7.6 | 13 | 7.6 | 81.9 |
|  | 72 | 16 | 6.9 | 12 | 7.4 | 83.3 |
|  | 90 | 17 | — | 17 | — | 81.1 |

EXAMPLE 4

Aerobic treatment of sanitary waste water

Using an apparatus as shown in FIG. 2, which is provided with a distributor as shown in FIG. 3 at the upper end of the draft tube, the BOD removal by aerobic bacteria of sanitary waste water was experimented. The experimental procedure and the result are shown below.

Apparatus for aerobic treatment: Made of polyvinyl chloride $15.7^{cm\phi} \times 1.7^{mH}$
  Volume about 30 liters
  Draft tube $5^{cm\phi} \times 1.5^{mH}$
  (The distributor disposed at the upper end of the draft tube consists of 4 trough-shaped arms extending in 4 directions)
Particulate carrier: Foamed polypropylene (with creasy surface)
  Columnar shape $3^{mm\phi} \times 3^{mmL}$
  Specific gravity 0.7
  Packed volume 10 liters
Kind of waste water: The sanitary waste water treated in a septic tank was used as the raw water
BOD of waste water: Shown in Table 4
Circulation of the water to be treated: Internal circulation made in such a way that the waste water rising up through the draft tube by aeration is distributed on the surface of the water by means of a distributor and allowed to go down through between the draft tube and the outer column of the treating apparatus.

The result is shown in Table 4.

In the present example, in which use was made of foamed polypropylene as foamed plastic material, there occurred no phenomenon that the carrier settles down due to the penetration of water and the attachment of microbes as encountered in the case of perlite in Example 1, and as a result all the foamed polypropylene particles in the apparatus could be used efficiently.

TABLE 4

| | Raw Water | | | Water treated | | Rate of removal |
|---|---|---|---|---|---|---|
| Flow rate (1/hr) | BOD (ppm) | Water temperature (°C.) | pH | BOD (ppm) | pH | of BOD (%) |
| 3.5 | 55 | 19 | 8.0 | 4 | 7.8 | 93 |
| " | 85 | 22 | 7.9 | 10 | 6.7 | 88 |
| 7.0 | 137 | 20 | 7.8 | 9 | 7.2 | 93 |
| " | 95 | 17 | 7.9 | 12 | 7.7 | 87 |
| 14.7 | 100 | 19 | 7.9 | 18 | 8.1 | 82 |
| " | 176 | 15 | 7.9 | 24 | 8.1 | 86 |

EXAMPLE 5

Denitrification of sanitary waste water subjected to nitrification

Use was made of an apparatus for denitrification as shown in FIG. 1 which was provided with a distributor of trough type as shown in FIG. 3 at the upper end of its draft tube.

By installing a stirrer within the draft tube an upflow was produced. In this treatment there was no provision for aeration because of anaerobic treatment.

As the particulate carrier of microbes use was made of foamed polypropylene particles. Methanol was added to the raw water in an amount 3 times as much as the NO$_3$—N.

Apparatus for anaerobic denitrification:
  Made of polyvinyl chloride $15.7^{cm\phi} \times 1.7^{mH}$
  Volume about 30 liters
  Draft tube $5^{cm\phi} \times 1.5^{mH}$
  The distributor disposed at the upper end of the draft tube consists of 4 trough-shaped arms extending in 4 directions. A cover with an air escape was mounted on the top of the apparatus.
Particulate carrier:
  Foamed polypropylene (with creasy surface)
  Columnar shape $1^{mm\phi} \times 2^{mmL}$
  Specific gravity 0.5
  Packed volume 10 liters
Kind of waste water:
  Sanitary waste water which was treated in a septic tank and then completely nitrified by aerobic treatment During the treatment no carrier settled down, so that in no case they could not be used. The result of the experiment is shown in Table 5.

TABLE 5

| | Raw Water | | | Water treated | | Rate of removal |
|---|---|---|---|---|---|---|
| Flow rate (1/hr) | NO$_3$—N (ppm) | Water temperature (°C.) | pH | NO$_3$—N (ppm) | pH | of NO$_3$—N (%) |
| 20 | 54 | 22 | 7.2 | <1 | 8.7 | >98 |
| " | 54 | 20 | 7.4 | <1 | 8.7 | >98 |
| 40 | 51 | 23 | 6.9 | <1 | 8.8 | >98 |
| " | 26 | 19 | 7.2 | <1 | 9.2 | >96 |
| 60 | 62 | 20 | 7.0 | 11 | 8.4 | 82 |
| " | 61 | 21 | 6.9 | 12 | 8.8 | 80 |
| " | 38 | 18 | 7.3 | <1 | 9.0 | >97 |

What is claimed is:

1. A process for biological treatment of waste water, comprising:
   (a) placing particulate material in water within a reactor, said particulate material having an apparent specific gravity smaller than the specific gravity of water making it possible for said particulate material to float on water;
   (b) allowing microbes to attach to said particulate material which acts as a carrier bed, floating in a substantially immersed state in said water;
   (c) distributing waste water in a uniform manner, downwardly into said carrier bed to form a fluidized bed of said carrier bed, in such a manner that the biological treatment of said waste water is achieved by contacting said waste water with said microbes while said waste water is passed through said fluidized bed;
   (d) removing treated water from a lower portion of said fluidized bed.

2. The process as defined in claim 1, wherein a portion of the treated water which has passed through the bed of said particulate carrier is returned to the top of said bed for reuse in circulation.

3. The process as defined in claim 1 or 2, wherein the excess microbe attached to the carrier is sloughed off by exerting shearing force upon the microbe-attached carrier.

4. The process as defined in any of claims 1 or 2, wherein said microbe is anaerobic bacteria or facultative anaerobic bacteria.

5. The process as defined in any of claims 1 or 2, wherein said microbe is aerobic bacteria, and an additional step is involved in that air or an oxygen-containing gas is supplied to the system from the lower part of said bed of carrier.

6. The process as defined in any of claims 1 or 2, wherein said particulate material is comprised of foamed plastic particles whose surfaces have been made creasy and of a mixture of lightweight foamed inorganic material therewith.

7. A process for biological treatment of waste water as in claim 1, further comprising:

introducing a gas into a draft tube provided in said reactor from a lower portion of said reactor in order to form an upward flow in said draft tubes in such a manner that carrier particles which are precipitated by the over attaching of microbes are sucked into said draft tubes;

stripping away said over attached microbes from said carrier by means of bubbles of said gas blown into said tube and by means of an upward flow of water within said tube; and returning said carrier to said fluidized bed.

* * * * *